United States Patent [19]

Pierantozzi

[11] Patent Number: 4,510,267

[45] Date of Patent: Apr. 9, 1985

[54] PREPARATION OF OLEFINS FROM SYNTHESIS GAS USING RUTHENIUM SUPPORTED ON CERIC OXIDE

[75] Inventor: Ronald Pierantozzi, Macungie, Pa.

[73] Assignee: Air Products and Chemicals, Inc., Allentown, Pa.

[21] Appl. No.: 573,433

[22] Filed: Mar. 5, 1984

Related U.S. Application Data

[63] Continuation of Ser. No. 373,934, May 3, 1982, abandoned.

[51] Int. Cl.$^3$ .................................................. C07C 1/04
[52] U.S. Cl. .................................... 518/715; 502/304
[58] Field of Search ......................................... 518/715

[56] References Cited

U.S. PATENT DOCUMENTS

| | | |
|---|---|---|
| 2,250,421 | 7/1941 | Riblett . |
| 2,623,058 | 10/1947 | Mattox . |
| 4,042,614 | 8/1977 | Vannice et al. . |
| 4,116,994 | 9/1978 | Vannice et al. . |
| 4,171,320 | 10/1979 | Vannice et al. . |
| 4,199,522 | 4/1980 | Murchison et al. . |
| 4,206,134 | 6/1980 | Kugler et al. . |
| 4,239,499 | 12/1980 | Pfefferle . |
| 4,261,864 | 4/1981 | Hargis . |
| 4,261,865 | 4/1981 | Hargis . |

FOREIGN PATENT DOCUMENTS

| | | |
|---|---|---|
| 1050051 | 3/1979 | Canada . |
| 1053266 | 4/1979 | Canada . |

*Primary Examiner*—Howard T. Mars
*Attorney, Agent, or Firm*—Michael Leach; E. Eugene Innis; James C. Simmons

[57] ABSTRACT

A catalyst comprising a ruthenium carbonyl compound deposited on a cerium oxide-containing support material provides for the selective synthesis of low molecular weight olefinic hydrocarbons from mixtures of hydrogen and carbon monoxide.

10 Claims, No Drawings

PREPARATION OF OLEFINS FROM SYNTHESIS GAS USING RUTHENIUM SUPPORTED ON CERIC OXIDE

The Government of the Unites States of America has rights in this invention pursuant to Contract No. DE-AC22-80PC30021 awarded by the U.S. Department of Energy.

This is a continuation of application Ser. No. 373,934, filed May 3, 1982, now abandoned.

TECHNICAL FIELD

The invention relates to the preparation of hydrocarbons by reacting carbon monoxide and hydrogen in the presence of a catalyst. More particularly, the invention relates to the selective synthesis of olefins from carbon monoxide and hydrogen using a ruthenium catalyst.

BACKGROUND OF THE INVENTION

Ruthenium catalysts have been known for many years to be the most active of the Group VIII metals in the carbon monoxide/hydrogen synthesis reaction. At low temperatures and very high pressures ruthenium can produce high molecular weight paraffinic waxes. At about atmospheric pressure methane is the principle product. Because it is such a good hydrogenation catalyst, ruthenium, until recently, has not been noted for its capacity to produce olefins.

U.S. Pat. No. 2,250,421 discloses a method for preparing liquid hydrocarbons from synthesis gas mixtures in which a metal carbonyl is decomposed at high temperatures in an inert hydrocarbon oil to yield finely divided metal forming a colloidal suspension. It is also taught that the metal carbonyl can be decomposed in the presence of a solid promoter and no inert hydrocarbon oil to directly deposit on the promoter. Mentioned as suitable metal carbonyls are the carbonyl compounds of iron, cobalt, chromium, molybdenum, tungsten, and ruthenium. Suggested promoting agents are alumina, thoria, ceria, manganese oxide, combinations thereof, and the like.

U.S. Pat. No. 2,623,058 discloses a process for preparing liquid hydrocarbons from carbon monoxide and hydrogen using a catalyst prepared by reacting an active metal of Groups VI or VIII of the Periodic Table with carbon monoxide to form a volatile carbonyl compound and decomposing the carbonyl compound on an essentially inactive readily fluidizable carrier material which may be a substance containing silica, alumina or magnesia in various combinations. A promoter such as the oxides of chromium, zinc, aluminum, magnesium, manganese and the rare earth metals may be incorporated into the carrier material.

U.S. Pat. No. 4,042,614 discloses a method for synthesizing $C_2$-$C_{10}$ olefinic hydrocarbons with reduced wax formation using a catalyst comprising ruthenium on titanium dioxide. Suitable ruthenium salts such as ruthenium chloride, ruthenium nitrate or ruthenium acetate may be used in preparing the ruthenium catalyst.

U.S. Pat. No. 4,171,320 discloses a method for the synthesis of hydrocarbons with reduced methane formation and for the selective production of $C_2$-$C_5$ olefinic hydrocarbons using as a catalyst ruthenium on a support comprising a Group VB metal oxide. As in the previous patent any suitable ruthenium salt may be used in preparing the catalyst.

U.S. Pat. No. 4,199,522 discloses the preparation of $C_2$-$C_4$ olefins by contacting carbon monoxide and hydrogen with a catalyst consisting essentially of at least one material selected from the group consisting of the sulfide, oxide or metal of molybdenum, tungsten, rhenium, ruthenium, nickel, palladium, rhodium, osmium, iridium and platinum and at least one material selected from the group consisting of the hydroxide, oxide or salt of an alkali metal, an alkaline earth metal or thorium.

U.S. Pat. No. 4,206,134 discloses a method for the selective synthesis of low molecular weight olefins using as a catalyst ruthenium on a manganese oxide support. Again, any suitable ruthenium salt may be used in the preparation of the catalyst.

Other patents which teach the selective synthesis of olefinic hydrocarbons by reacting carbon monoxide and hydrogen in the presence of a catalyst include U.S. Pat. Nos. 4,116,994; 4,261,864; 4,261,865 and Canadian Pat. Nos. 1,050,051 and 1,053,266.

U.S. Pat. No. 4,239,499 teaches producing a fuel gas containing a high proportion of methane by passing methanol over a metal catalyst such as ruthenium on alumina which may be stabilized by ceria or thoria.

SUMMARY OF THE INVENTION

The invention provides a process for the selective synthesis of olefins by reacting hydrogen and carbon monoxide under reaction conditions over a ruthenium catalyst. The ruthenium catalyst is prepared by depositing a ruthenium carbonyl compound on a ceric oxide-containing support. The catalyst is unusually selective for the production of olefins with a low methane yield from synthesis gas having a low hydrogen:carbon monoxide ratio.

DETAILED DESCRIPTION OF THE INVENTION

A method is provided for the selective synthesis of olefinic hydrocarbons, particularly $C_2$-$C_6$ olefins, from hydrogen and carbon monoxide at pressures from about 100 to $10^5$ kPa. The method comprises passing a synthesis gas stream comprising hydrogen and carbon monoxide at a $H_2$:CO molar ratio ranging from 1:2 to 2:1, preferably 1:1, at a space velocity of about 100 $hr^{-1}$ to 10,000 $hr^{-1}$ over a catalyst comprising from 0.01 to 15 wt. % ruthenium on $CeO_2$ or other ceric oxide-containing materials for a time sufficient to effect the generation of the desired olefinic hydrocarbon products.

Contemplated as the functional, or operative, equivalent of carbon monoxide in this invention is carbon dioxide.

Suitable process temperatures range from about 200° to 400° C., preferably 320° to 360° C., and suitable pressures range from about 100 to $10^5$ kPa, preferably 100 to $2.4 \times 10^3$ kPa. The process temperature should be at least about 200° C. in order to decompose the ruthenium carbonyl compounds on the ceric oxide-containing supports. Workers skilled in the art will understand that ruthenium carbonyl compounds which volatilize under the process conditions are not suited for practicing the invention.

Ruthenium supported on $CeO_2$ or other ceric oxide-containing supports results in a catalyst system which exhibits superior olefinic hydrocarbon synthesis characteristics while suppressing the production of methane. The ceric oxide-containing supports which may be used in the practice of the invention are selected from the group comprising $CeO_2$, $Al_2O_3$-$CeO_2$, $SiO_2$-$CeO_2$, $CeO_2$-carbon $CeO_2$-rare earth oxides and the like.

With most supported metal catalysts, the higher the surface area of the support, the higher the dispersion of the supported metal at a given metal loading. It is therefore generally desirable to use a ceric oxide-containing support with as high a surface area as possible to maximize the dispersion of the ruthenium metal. The ceric oxide support used in the following examples had a relatively low surface area of about 1 m²/g. Nevertheless, conversions were good and would probably improve using a ceric oxide support of greater surface area. Without wishing to be held to any particular theory, it is believed that the invention advantageously affords such a high dispersion of the supported ruthenium metal by using a ruthenium carbonyl compound deposited on the ceric oxide-containing support. It is believed that the ruthenium carbonyl compound is decomposed on the ceric oxide-containing support under the process conditions to give a highly dispersed ruthenium metal catalyst. This high degree of dispersion combined with the ceric oxide helps to suppress the hydrogenation ability of the catalyst resulting in high selectivities to olefins, particularly $C_2$-$C_6$ olefins, compared with ruthenium catalysts of the prior art which are supported on materials such as $Al_2O_3$, MgO and the like.

The ruthenium catalysts employed in the practice of the invention can be prepared by techniques known in the art for the preparation of other catalyst systems. A suitable ruthenium carbonyl compound such as, for example, $[Ru_3(CO)_{12}]$, $[H_4Ru_4(CO)_{12}]$, $[H_2Ru_6(CO)_{18}]$ or $[Ru_6C(CO)_{17}]$ is dissolved in a solvent such as cyclohexane or any suitable solvent and stirred with the chosen ceric oxide-containing support which preferably has been dried under vacuum prior to use. After thorough mixing, the solvent is removed in vacuum at room temperature. The catalyst is then protected from the air by keeping it in a controlled atmosphere at all times. It is not necessary that the catalyst undergo any pretreatment prior to reaction with the hydrogen and carbon monoxide mixture.

$[Ru_3(CO)_{12}]$ may be purchased from Strem Chemicals. $[H_4Ru_4(CO)_{12}]$, $[H_2Ru_6(CO)_{18}]$ and $[Ru_6C(CO)_{17}]$ may be prepared according to literature procedures in *J. Amer. Chem. Soc.* 1975, 97 (14) p3942; *J. Chem. Soc., Chem. Comm.* 1979, p735; and *J. Organomet Chem.* 1980, 191 pC3.

EXAMPLE 1

The catalyst was prepared by dissolving 0.5 g of the ruthenium carbonyl compound $[Ru_3(CO)_{12}]$ in 8 ml cyclohexane, sufficient to wet the entire surface of 10 g $CeO_2$ (purchased from Cerac) which had been dried at 200° C. under vacuum prior to use. The cyclohexane solution of the ruthenium carbonyl compound was then contacted with the $CeO_2$ and the solvent removed in vacuum leaving behind the metal carbonyl compound on the support. The infrared spectrum of the solid showed that the ruthenium carbonyl compound was unchanged on the ceric oxide support; e.g. $[Ru_3(CO)_{12}]$ exhibits $\nu_{C=O}$ bands in the infrared spectrum at 2060, 2030 and 2010 cm⁻¹ while $[Ru_3(CO)_{12}]/CeO_2$ exhibited $\nu_{C=O}$ bands at 2057, 2017 and 1995 cm⁻¹.

Without undergoing any pretreatment 9.49 g of the catalyst containing 2.32% ruthenium by weight was placed in a fixed bed reactor for Runs 1-4 and synthesis gas was passed over the catalyst using the process conditions shown in Table 1. Also shown in Table 1 are the conversions of hydrogen and carbon monoxide. The product distribution data obtained from these runs are shown in Table 2.

Run 1, which was performed at 352° C., 2100 kPa, a space velocity of 239 hr⁻¹ and a hydrogen:carbon monoxide ratio of about 1, showed an overall selectivity to olefins of about 55.5%, with $C_2$-$C_4$ olefins at 32.8% and $C_2$-$C_6$ olefins at 46.6%. The methane yield was only 12.5%.

When the space velocity was increased to 835 hr⁻¹ in Run 2, the product distribution data showed the olefin selectivity had increased to 65.1%, with $C_2$-$C_4$ olefins at 34.8% and $C_2$-$C_6$ olefins at 49.3%. With respect to alkane production the methane selectivity was 12.3%, $C_2$-$C_4$ alkanes were 3.8% and $C_2$-$C_6$ alkanes were about 4.9%.

When the pressure was increased to 6,300 kPa in Run 3, the olefin selectivity was 54.9%, with $C_2$-$C_4$ olefins at 29.9% and $C_2$-$C_6$ olefins at 42.3%. The alkane yield comprised a low methane yield of 8.7%, $C_2$-$C_4$ alkanes at 7% and $C_2$-$C_6$ alkanes at 10.5%.

When the hydrogen:carbon monoxide molar ratio was increased to 2:1 with a space velocity of 712 hr⁻¹, the methane yield increased to 27.2% and the olefin selectivity decreased to 29.5%, with $C_2$-$C_4$ olefins at 24.9% and $C_2$-$C_6$ olefins at 28.8%. The corresponding alkane production was $C_2$-$C_4$ alkanes at 15.1% and $C_2$-$C_6$ alkanes at 22.4%.

The above data demonstrates that $[Ru_3(CO)_{12}]$ catalyst on cerium oxide support was highly selective for low molecular weight olefins while concomitantly affording low yields of methane.

TABLE 1

| Run | CATALYST | °C. | kPa | GHSV | H₂:CO | % H₂ Conv. | % CO Conv. |
|---|---|---|---|---|---|---|---|
| 1 | Ru₃(CO)₁₂/CeO₂ | 352 | 2100 | 239 | 1 | 31.6 | 28.1 |
| 2 | Ru₃(CO)₁₂/CeO₂ | 353 | 2100 | 835 | 1 | 35.6 | 23.3 |
| 3 | Ru₃(CO)₁₂/CeO₂ | 353 | 6300 | 239 | 1 | 87.0 | 63.0 |
| 4 | Ru₃(CO)₁₂/CeO₂ | 353 | 2100 | 712 | 2 | 28.1 | 22.4 |
| 5 | H₄Ru₄(CO)₁₂/CeO₂ | 354 | 2100 | 207 | 1 | 54.2 | 20.8 |
| 6 | H₄Ru₄(CO)₁₂/CeO₂ | 354 | 2100 | 546 | 1 | 14.8 | 9.6 |
| 7 | H₄Ru₄(CO)₁₂/CeO₂ | 354 | 2100 | 583 | 2 | 15.7 | 3.3 |
| 8 | H₄Ru₄(CO)₁₂/CeO₂ | 354 | 6300 | 609 | 1 | 43.4 | 11.5 |
| 9 | RuCl₃/CeO₂ | 351 | 2100 | 314 | 1 | | 84.6 |
| 10 | Ru₃(CO)₁₂/Al₂O₃ | 261 | 2100 | 800 | 1 | | 39.8 |
| 11 | Ru₃(CO)₁₂/Al₂O₃ | 344 | 2100 | 1257 | 1 | | 87.4 |
| 12 | Ru₃(CO)₁₂/MgO | 315 | 2100 | 262 | 1 | | 33.6 |

TABLE 2

| Product Carbon Number | Run 1 n-alkane wt % | Run 1 l-alkene wt % | Run 2 n-alkane wt % | Run 2 l-alkene wt % | Run 3 n-alkane wt % | Run 3 l-alkene wt % | Run 4 n-alkane wt % | Run 4 l-alkene wt % | Run 5 n-alkane wt % | Run 5 l-alkene wt % | Run 6 n-alkane wt % | Run 6 l-alkene wt % |
|---|---|---|---|---|---|---|---|---|---|---|---|---|
| $C_1$ | 12.5 | — | 12.3 | — | 8.7 | — | 27.2 | — | 12.7 | — | 15.5 | — |
| $C_2$ | 2.6 | 4.9 | 0.9 | 7.7 | 1.7 | 5.7 | 6.6 | 4.9 | 1.9 | 6.8 | 1.5 | 9.1 |
| $C_3$ | 1.9 | 16.4 | 1.4 | 15.2 | 2.3 | 13.6 | 3.8 | 14.9 | 1.7 | 14.8 | 1.9 | 17.5 |
| $C_4$ | 4.6 | 11.5 | 1.5 | 11.9 | 3.0 | 10.6 | 4.8 | 5.1 | 2.3 | 9.8 | 1.9 | 12.1 |
| $C_5$ | 3.8 | 7.9 | 1.1 | 7.8 | 2.2 | 7.1 | 4.5 | 2.5 | 1.5 | 6.2 | 1.3 | 7.5 |
| $C_6$ | 2.5 | 5.9 | trace | 6.7 | 1.3 | 5.3 | 2.9 | 1.4 | 1.5 | 4.5 | 0.8 | 5.0 |
| $C_7$ | 1.6 | 3.1 | 0.8 | 4.0 | 2.3 | 3.6 | 1.6 | 0.7 | 0.9 | 2.7 | 0.4 | 2.9 |
| $C_8$ | 1.4 | 1.8 | 0.6 | 2.4 | 1.5 | 2.2 | 0.6 | — | 0.9 | 2.0 | 0.7 | 2.2 |
| $C_9$ | 1.0 | 1.4 | 0.3 | 1.7 | 1.2 | 1.6 | 0.4 | — | 0.7 | 1.6 | 0.4 | 1.5 |
| $C_{10}$ | 0.7 | 1.0 | 0.4 | 1.3 | 0.9 | 1.3 | 0.3 | — | 0.5 | 1.4 | 0.3 | 1.0 |
| $C_{11+}$ | 3.2 | 1.6 | 2.4 | 6.5 | 2.3 | 3.9 | 0.3 | — | 5.0 | 5.6 | 1.8 | 3.1 |
| MeOH | 0.6 | | — | | 1.6 | | 1.0 | | — | | | |
| EtOH | — | | 2.4 | | 3.5 | | 7.3 | | 3.6 | | 3.6 | |
| Total HC | | 55.5 | | 65.1 | | 54.9 | | 29.5 | | 55.2 | | 61.9 |

| Product Carbon Number | Run 7 n-alkane wt % | Run 7 l-alkene wt % | Run 8 n-alkane wt % | Run 8 l-alkene wt % | Run 9 n-alkane wt % | Run 9 l-alkene wt % | Run 10 n-alkane wt % | Run 10 l-alkene wt % | Run 11 n-alkane wt % | Run 11 l-alkene wt % | Run 12 n-alkane wt % | Run 12 l-alkene wt % |
|---|---|---|---|---|---|---|---|---|---|---|---|---|
| $C_1$ | 26.0 | — | 11.5 | — | 35.7 | — | 54.8 | — | 86.7 | — | 65.6 | — |
| $C_2$ | 2.7 | 10.3 | 1.7 | 4.6 | 5.8 | 0 | 4.1 | 5.7 | 4.9 | 0.3 | 13.5 | 0.3 |
| $C_3$ | 2.2 | 16.3 | 1.7 | 9.1 | 2.5 | 0.7 | 1.0 | 9.1 | 1.7 | 1.9 | 8.1 | 1.4 |
| $C_4$ | 1.8 | 9.2 | 2.1 | 7.0 | 2.4 | 0.5 | 2.9 | 4.5 | 1.5 | 0.6 | 5.3 | 0.9 |
| $C_5$ | 1.2 | 4.9 | 1.6 | 5.0 | 1.3 | 0.4 | 2.1 | 2.7 | 0.9 | 0.2 | 3.1 | 0.4 |
| $C_6$ | 0.7 | 2.9 | 3.1 | 3.1 | 0 | | 2.0 | 0 | 0.3 | 0.6 | 1.1 | 0 |
| $C_7$ | 0.5 | 1.5 | 1.0 | 2.4 | | | 0.6 | 0 | | | | |
| $C_8$ | 0.5 | 0.9 | 0.7 | 1.9 | | | 2.0 | 0 | | | | |
| $C_9$ | 0.4 | 0.8 | 1.2 | 1.7 | | | 0.4 | 0 | | | | |
| $C_{10}$ | trace | 0.4 | 1.1 | 1.5 | | | 0.3 | 0 | | | | |
| $C_{11+}$ | 1.9 | 2.9 | 11.0 | 15.8 | | | 4.0 | | | | | |
| MeOH | | | 1.7 | | 34.1 | | | | | | | |
| EtOH | 7.0 | | 1.3 | | 5.5 | | | | | | | |
| Total HC | | 44.8 | | 52.0 | | 1.6 | | 22.0 | | 3.6 | | 3.0 |

EXAMPLE 2

A catalyst was prepared as described in Example 1 using [H$_4$Ru$_4$(CO)$_{12}$] as the ruthenium carbonyl compound. The catalyst contained 0.38% ruthenium by weight. The catalyst (12.61 g) was tested in Runs 5–8 under the conditions set forth in Table 1 with the product distribution data set forth in Table 2.

Run 5 at a space velocity of 207 hr$^{-1}$, 354° C. 2100 kPa and a hydrogen:carbon monoxide molar ratio of about 1 gave a product distribution comprising 12.7% methane and 55.2% olefins. The C$_2$–C$_4$ olefin fraction was 31.4% and the C$_2$–C$_6$ olefin fraction was 42.1%. The corresponding alkanes were 5.9% for the C$_2$–C$_4$ fraction and 8.9% for the C$_2$–C$_6$ fraction.

At the higher space velocity of 546 hr$^{-1}$ in Run 6 the methane yield increased to 15.5%, but the olefin yield also increased to 61.9%, with C$_2$–C$_4$ olefins at 38.7% and C$_2$–C$_6$ olefins at 51.2% of the total hydrocarbon product.

When the hydrogen:carbon monoxide ratio was increased to 2:1 in Run 7, the methane yield increased to 26% and the olefin selectivity decreased to 44.8%.

At 6,300 kPa and a space velocity of 609 hr$^{-1}$ in Run 8, the methane yield was only 11.5% and olefin selectivities of 52% were achieved with an overall shift to higher molecular weight hydrocarbons.

It can be seen from Runs 5–8 that [H$_4$Ru$_4$(CO)$_{12}$] on ceric oxide support was highly selective to the production of C$_2$–C$_6$ olefinic hydrocarbons while maintaining a low production of methane.

EXAMPLE 3

This example illustrates that a ruthenium carbonyl compound is necessary for the observed olefin selectivities. A catalyst was prepared by contacting an aqueous solution of 0.39 g RuCl$_3$.3H$_2$O in 35 ml water with 30 g ceric oxide. Removal of the water yielded a catalyst containing 0.62% ruthenium by weight. The catalyst was dried in an air stream at 110° C. for 8 hours. The catalyst was then reduced in hydrogen at atmospheric pressure and 450° C. for 2 hours. The catalyst was tested as Run 9 under the conditions shown in Table 1 affording the product distribution shown in Table 2. The methane yield was 35.7% with a low olefin selectivity of 1.6%. Selectivity toward the formation of oxygenated products was 41.8% including 1.1% dimethyl ether and 1.1% propanol.

EXAMPLE 4

This example demonstrates the need for a ceric oxide support. A catalyst was prepared according to the procedure of Example 1 using alumina and magnesium oxide as the support material in place of ceric oxide. The catalysts contained 1.94% ruthenium on alumina in Runs 10 and 11 and 0.42% ruthenium on magnesium oxide in Run 12 and were tested at the conditions shown for Runs 10, 11 and 12 in Table 1.

Table 2 shows that the alumina supported catalyst in Run 10 produced a methane yield of 54.8% at 261° C. and a relatively low olefin yield of 22.0%. The primary products of this run were saturated hydrocarbons. At 344° C. in Run 11 the methane yield was 86.7% with only a 3.6% olefin yield.

In Run 12 the magnesium oxide supported ruthenium carbonyl compound gave primarily methane as the product. The conversion of carbon monoxide was 33.6% with a 65.6% methane yield and a low 3.0 olefin yield.

STATEMENT OF INDUSTRIAL APPLICATION

The invention provides a process for preparing valuable low molecular weight olefinic hydrocarbons by reacting a mixture of hydrogen and carbon monoxide over a ruthenium carbonyl compound supported on a ceric oxide-containing material. These olefins are useful chemical intermediates for the production of plastics, rubber, alcohols, ketones, aldehydes, esters and acids.

I claim:

1. In a process for the synthesis of hydrocarbons by reacting hydrogen and carbon monoxide over a ruthenium-containing catalyst, the method for selectively synthesizing olefins which comprises reacting the hydrogen and carbon monoxide under reaction conditions over a ruthenium catalyst made by preparing a solution of a ruthenium carbonyl compound in a solvent sufficient to wet the surface of a ceric oxide-containing support selected from the grouup consisting of $CeO_2$, $Al_2O_3$-$CeO_2$, $SiO_2$-$CeO_2$, $CeO_2$-carbon or $CeO_2$-other rare earth oxides, contacting the ceric oxide-containing support with the ruthenium carbonyl compound-containing solution and removing the solvent to yield the ruthenium carbonyl compound deposited on the ceric oxide-containing support.

2. The method of claim 1 wherein the ceric oxide-containing support is $CeO_2$.

3. The method of claim 1 wherein the ruthenium carbonyl compound is $[Ru_3(CO)_{12}]$, $[H_4Ru_4(CO)_{12}]$, $[H_2Ru_6(CO)_{18}]$ or $[Ru_6C(CO)_{17}]$.

4. The method of claim 1 wherein the reaction is performed at a $H_2$:CO molar ratio from 1:2 to 2:1, a space velocity of 100 to 10,000 $hr^{-1}$, a temperature from 200° to 400° C. and a pressure from 100 to $10^5$ kPa.

5. The method of claim 1 wherein the catalyst comprises from 0.01 to 15 wt. % ruthenium.

6. The method of claim 1 wherein the temperature is at least about 200° C.

7. A method for selectively synthesizing olefins which comprise reacting hydrogen and carbon monoxide at a $H_2$:CO molar ratio from 1:2 to 2:1, a space velocity of 100 to 10,000 $hr^{-1}$, a temperature from 320° to 360° C. and a pressure from 100 to $2.4 \times 10^3$ kPa over a ruthenium catalyst comprising $[Ru_3(CO)_{12}]$ or $[H_4Ru_4(CO)_{12}]$ deposited on a ceric oxide, the catalyst made by preparing a solution of the ruthenium carbonyl compound in a solvent sufficient to wet the surface of the ceric oxide, contacting the ceric oxide with the ruthenium carbonyl compound-containing solution and removing the solvent to yield the ruthenium carbonyl compound on the ceric oxide.

8. The method of claim 4 wherein the catalyst comprises from 0.01 to 15 wt% ruthenium.

9. The method of claim 4 wherein the $H_2$:CO molar ratio is about 1:1.

10. The method of claim 7 wherein the $H_2$:CO molar ratio is about 1:1.

* * * * *